US009365817B2

United States Patent
Benedetti et al.

(10) Patent No.: US 9,365,817 B2
(45) Date of Patent: Jun. 14, 2016

(54) **DRIED AND/OR MICROENCAPSULATED *SACCHAROMYCES CEREVISIAE* CELLS WITH A HIGH CONTENT OF (S)-(+)-S-ADENOSYL-L-METHIONINE, PROCESS FOR THEIR PREPARATION, AND COMPOSITONS CONTAINING SAID CELLS**

(75) Inventors: Alberto Benedetti, Cernusco sul Naviglio (IT); Lino Sivieri, Olginate (IT)

(73) Assignee: Gnosis S.p.A., Desio (IT)

( * ) Notice: Subject to any disclaimer, the term of this patent is extended or adjusted under 35 U.S.C. 154(b) by 2010 days.

(21) Appl. No.: 11/921,758

(22) PCT Filed: Jun. 9, 2006

(86) PCT No.: PCT/EP2006/005521
§ 371 (c)(1),
(2), (4) Date: Aug. 13, 2009

(87) PCT Pub. No.: WO2006/131382
PCT Pub. Date: Dec. 14, 2006

(65) Prior Publication Data
US 2010/0028315 A1 Feb. 4, 2010

(30) Foreign Application Priority Data
Jun. 9, 2005 (EP) ..................... 05425413

(51) Int. Cl.
C12N 1/18 (2006.01)
C12N 1/04 (2006.01)
A61K 9/20 (2006.01)
A61K 9/28 (2006.01)

(52) U.S. Cl.
CPC ............... *C12N 1/04* (2013.01); *A61K 9/2009* (2013.01); *A61K 9/2013* (2013.01); *A61K 9/2054* (2013.01); *A61K 9/282* (2013.01); *A61K 9/2846* (2013.01); *C12N 1/18* (2013.01)

(58) Field of Classification Search
None
See application file for complete search history.

(56) References Cited

U.S. PATENT DOCUMENTS

| 4,562,149 A | 12/1985 | Shiozaki et al. |
| 5,100,786 A | 3/1992 | Shiomi et al. |
| 7,157,258 B2 * | 1/2007 | Durand et al. ............... 435/177 |
| 2004/0063660 A1 | 4/2004 | Hebert |

FOREIGN PATENT DOCUMENTS

WO WO0190130 A 11/2001

OTHER PUBLICATIONS

"Stabilization of S-adenosyl-L-methionine promoted by trehalose." Morana Alessandra et al. Biochimica et Biophysica Acta, Nov. 14, 2002 vol. 1573, No. 2, pp. 105-108.
"Inusual Intracellular Accumulation of S. Adenosyl-L-Methionine by Microorganisms" Shiozaki S. et al. Agricultural and Bilogical Chemistry, vol. 48, No. 9, 1984, pp. 2293-2300.

* cited by examiner

*Primary Examiner* — Irene Marx
(74) *Attorney, Agent, or Firm* — Amin Talati & Upadhye, LLC; George M. Carrera, Jr.; Yichen Cao

(57) ABSTRACT

Disclosed are dried and/or microencapsulated *Saccharomyces cerevisiae* cells with a high content of (S)-(+)-S-adenosyl-L-methionine, in the form of a free base obtainable from selected high-productivity strains of (S)-(+)-SAMe.

7 Claims, No Drawings

DRIED AND/OR MICROENCAPSULATED SACCHAROMYCES CEREVISIAE CELLS WITH A HIGH CONTENT OF (S)-(+)-S-ADENOSYL-L-METHIONINE, PROCESS FOR THEIR PREPARATION, AND COMPOSITONS CONTAINING SAID CELLS

CROSS-REFERENCE TO RELATED APPLICATION

This application is a National Stage entry of International Application No. PCT/EP2006/005521, filed Jun. 9, 2006, the entire specification claims and drawings of which are incorporated herewith by reference.

This invention relates to dried and/or microencapsulated Saccharomyces cerevisiae cells with a high content of (S)-(+)-S-adenosyl-L-methionine, a process for their preparation, and compositions containing said cells.

In particular, the invention relates to Saccharomyces cerevisiae cells wherein the diastereoisomer, free base, (R)-(+)-S-adenosyl-L-methionine (hereinafter called (R)-(+)-SAMe) is in a quantity lower than or equal to 10% of the diastereoisomer, free base, (S)-(+)-S-adenosyl-L-methionine (hereinafter called (S)-(+)-SAMe).

BACKGROUND TO THE INVENTION

It is known that the (S)-(+)-SAMe ion is highly unstable and consequently rapidly degradable if extracted from the producing cells. In fact, many years passed between the discovery of SAMe (Cantoni et al. "Phosphorous metabolism", Baltimore 1952 2, 129; Cantoni et al. J. Biol. Chem, 1953, 204, 403) and its marketing. The stability problem was initially solved by salification, in particular in the form of sulphates. However, the sulphate salts of SAMe sometimes cause side effects, especially in the gastric mucosa, due to their inherent acidity.

It is known that (R, S) SAMe is a physiological donor of methyl groups involved in enzymatic reactions of transmethylation, which is present in all living organisms and has therapeutic effects on chronic liver disorders, adiposis, lipaemia and atherosclerosis.

It is also known (J. W. Cornforth, J.A.C.S., 1977, 99, 7292-7300; Stolowitz et al., J.A.C.S., 1981, 103, 6015-6019) that products containing (R, S) SAMe consist of a mixture of two diastereoisomers: (R)-(+)-SAMe and (S)-(+)-SAMe, which have the following molecular structure:

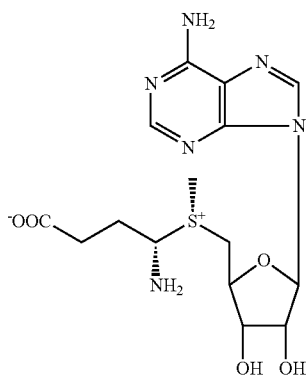

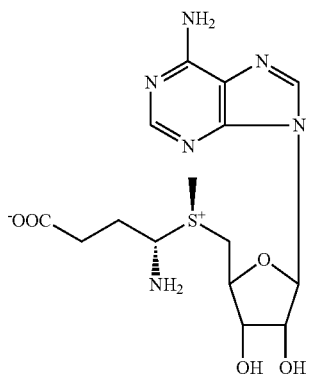

It has also been demonstrated (De La Haba et al., J.A.C.S. 1959, 81, 3975-3980) that only one of the two diastereoisomers, ie. (S)-(+)-SAMe, is enzymatically active by spontaneous transmethylation and racemisation, and consequently generates the formation of the inactive diastereoisomer (R)-(+)-SAMe amounting to approx. 20% (Wu et al., Biochemistry 1983, 22, 2828-2832).

It has been observed that in all the products available on the market containing SAMe, the inactive diastereoisomer (R)-(+)-SAMe is present in the amount of at least 20%; it has further been observed that said percentages increase over time to 40% and more due to spontaneous racemisation.

The cells have a natural content of (S)-(+)-SAMe equal to approx. 100%, but the industrial extraction and purification methodology produces a partly degraded product, and consequently a mixture of ≥20% (R)-(+)-SAMe and ≤0.80% (S)-(+)-SAMe These factors clearly confirm that the mixture of diastereoisomers is unstable over time, and this was already known in relation to the product in solution (G. L. Creason et al., Phytochemistry, vol. 24, N. 6, 1151-1155, 1985; H. C. Uzar, Liebigs Ann. Chem. 1989, 607-610).

It has also been observed that (R, S) SAMe, and its salified forms approved for pharmaceutical use, present problems of instability, in addition to the complexity of the preparation and purification processes.

Known purification processes involve the use of strong acid resins (JP 13680/1971), chelating resins (JP 20998/1978) or expensive special reagents, such as picric or picolinic acid (U.S. Pat. No. 3,707,536 and U.S. Pat. No. 3,954,726); however, they lead to partial racemisation of the SAMe sulphur and consequently to the production of end products containing the inactive diastereoisomer in an amount exceeding 20%.

However, purification processes involving the use of weak acid resins (JP 14299/1981, FR-A-2531714, EP-A-0141914) only allow partial separation of the active diastereoisomer to be obtained, and consequently a degree of purity insufficient for pharmaceutical purposes.

Although the performance of some of the said processes allows greater purity to be obtained, partial racemisation implies, in any event, that at least 20% of inactive diastereoisomer is present; moreover, in some cases (FR 2531714), potassium bicarbonate is used to extract the product from the cells, with consequent precipitation of potassium perchlorate, which causes difficulty with the separation and subsequent elimination of the product. In EP-A-0141914, the lysis of yeast cells containing SAMe is performed in the presence of an organic solvent (such as ethyl acetate, acetone, etc.), also using chromatographic columns which require the use of resins with a particle size of 100-200 mesh, involving heavy investments and maintenance costs for regeneration and washing.

The use of solvents to extract the SAMe necessarily involves the use of flameproof plant, solvent recovery and distillation systems, as well as the separation and necessary drying of the depleted biomass, to prevent it from being eliminated together with the residual solvent. All these factors clearly involve an increase in expenditure and the cost of the operations.

Morana et al., Biochimica Biophysica Acta, 1573 (2002), 105-108, disclose that SAMe may be stabilized by trehalose in lyophilized yeast extracts and, to a lesser extent, in lyophilized yeast cells. Lyophilization is however disadvantageous since the cells are subjected to stressful conditions (frozen at −20° C. and then thawed at 37° C.) and trehalose is anyhow presumed essential to stabilize intracellular SAMe. The addition of trehalose would moreover involve economical and regulatory problems.

There is consequently a need for derivatives or dosage forms of SAMe wherein the percentage of active (S)-(+)-SAMe diastereoisomer is clearly higher than the inactive (R)-(+)-SAMe isomer, and wherein the said percentage is stable over time. A further important goal would be a stable administration dosage form cf (S)-(+)-SAMe as a free base, without recurring to the formation of salts and/or to stabilizing agents and without subjecting yeast cells to stressful conditions.

DESCRIPTION OF THE INVENTION

It has now been discovered that SAMe free base is stable inside the producing cell even without the addition of stabilizing agents. The protection afforded by the intact cell wall of the yeast also promotes greater stability over time at ambient temperature.

This invention therefore relates to dried and/or microencapsulated *Saccharomyces cerevisiae* cells with a high content of (S)-(+)-S-adenosyl-L-methionine, in the form of a free base obtainable from yeast cells which are simply dried at temperatures ranging from 20 to 40° C., optionally under reduced pressure, in particular from *Saccharomyces cerevisiae* strains characterised by high-productivity of (S)-(+)-SAMe.

The cells according to the invention can be administered as such in suitable pharmaceutical forms, especially capsules, tablets, gastro-resistant tablets and the like.

Suitable strains of *Saccharomyces cerevisiae* can be selected by screening colonies originating from plating on YM agar a sample of culture broth taken from industrial fermentation at the pre-stationary stage, and subsequently checking its ability to produce (S)-(+)-SAMe.

The SAMe productivity of a strain thus selected, called GNL24/497, is 2.0%-6.0% w/dry weight, more specifically 3%-4% w/dry w, at the end of fermentation, and 7%-20% w/dry w, and more specifically 10%-16% w/dry w, at the end of the enrichment stage.

The yeast *Saccharomyces cerevisiae* GNL24/497 has been classified as such by the Perugia University "Industrial Yeast Collection DBVPG" on the basis of its morphophysiological characteristics and by the DNA-DNA reassociation technique. The strain *Saccharomyces cerevisiae* GNL 24/497, which has been deposited in the DBVPG collection for patent purposes according to the Treaty of Budapest dated 27 Apr. 2005, under access number DBVPG 8 P, constitutes a further subject of the invention.

The yeast is grown at industrial level according to known techniques and conditions, and used to prepare bread-making biomasses wherein DL methionine in the quantity of 0.5%-4.0% w/v, more specifically 1.0%-3.0% w/v, is added to ordinary culture medium based on molasses (F. Schlenk and R. E. De Palma, J. Biol. Chem. 1957 229, 1051; F. Schlenk, J. L. Dainko and S. M. Stanford, Archives of Biochemistry and Biophysics 1959, 83, 28-34).

The biomass is collected by centrifugation, washed, resuspended and subjected to a process of activation in a medium (hereinafter called "the activation medium") containing potassium phosphate; ammonium sulphate; sodium citrate; magnesium, manganese, zinc and calcium salts; glucose and L-methionine or DL-methionine (F. Schlenk and R. E. De Palma, J. Biol. Chem, 1957, 229, 1051-F. Schlenk et al., Enzymologia 29, 283, 1965).

The activation process can be repeated 2-5 times, more specifically 2-3 times, under sterile or non-sterile conditions; at atmospheric pressure or under slight pressure; at a controlled pH or free pH; with aeration of 0.1-1.5 v/v/m, or more specifically 0.2-1.0 v/v/m; at a temperature of 25° C.-35° C., or more specifically 28° C.-32° C.; for 6-24 h, or more specifically 8-18 h.

The biomass concentration in the activation medium can range from 2.5% to 18% dry weight/volume, and more specifically from 5%-15% dry weight/volume. After enrichment, the biomass is collected by centrifugation or microfiltration, washed several times with sterile water or phosphate buffer pH 5.2 (±0.2), and then dried or microgranulated according to conventional techniques.

According to a preferred aspect, the microgranulation can be performed by a process which comprises:
a) centrifugation or microfiltration of yeast cells from the culture broth;
b) washing with water of the yeast cells and resuspension in sterile water;
c) possibly, the addition to the suspension obtained in b) of bentonite, kaolin, silica, microcellulose, lecithinated sodium, and/or natural or hydrogenated vegetable or animal oils;
d) drying at low pressure of the mixture obtained in c) at a temperature of between 20° C. and 40° C. to an $H_2O$ content of between 0.5 and 5%;
e) addition of excipients to the dried substance and direct compression of the mixture;
f) granulation of the tablets obtained in e);
g) coating of the granules obtained in f) with molten wax.

This process is disclosed in European patent application no. 05425084.0 of 18.2.2005, filed by the Applicant.

The biomass of dried, microgranulated yeast is used to prepare tablets with a weight of between 1.0 and 2.5 g, and more specifically 1.3-1.8 g, having a content of the active constituent (S)-(+)-SAMe of between 100 and 400 mg, and more specifically between 150 and 300 mg. The tablets can be prepared according to known techniques using dried yeast with a high (S)-(+)-SAMe content or by adding excipients such as microcrystalline cellulose, silica, glycerol behenate, magnesium stearate (or the like). The tablets thus obtained can also be coated with excipients like BIOGAPRESS® VEGETAL, Labrafac® CC, EUDRAGIT L30D-55, titanium dioxide, talc, colloidal silicon dioxide, triethyl citrate, FD & C yellow 5, or the like, to standardise gastric resistance.

The invention is illustrated in greater detail in the examples below.

Example 1

The yeast *Saccharomyces cerevisiae* GNL-24/497 (DBVPG 8 P) is grown in an industrial medium based on molasses used for bread-making yeast, to which 30 g/l of DL-methionine has been added, for 24 h at 28° C. The biomass is collected by centrifugation and washed twice with tap water: creams with 20%±2 g/dry weight/vol. and a total SAMe content of 3% (±0.5%) w/dry w are obtained. In a 10-liter fermenter a medium is prepared containing:

glucose 82 g/l, DL-methionine 12 g/l, $Na_2NO_3$ 10 g/l, $KH_2PO_4$ 3.5 g/l, KOH 0.385 g/l, $(NH_4)_2SO_4$ 7.0 g/l, $MgSO_4$ 0.5 g/l, antifoam 0.03 g/l. The medium is heated to 28° C., and the creams are added until a concentration of 100 g/l dry weight is obtained. Activation conditions: agitation 200 rpm, air 0.25 v/v/min. At the end of glucose consumption, after approx. 12 h, the cells are collected by centrifugation, recovering 100-102 g/l dry weight of biomass containing 11.5% of total SAMe, of which 4.5% is (R)-(+)-SAMe isomer and 95.5% is (S)-(+)-SAMe isomer.

The biomass was dried at 28° C. to an $H_2O$ content ≤0.5% w/w.

Analysis confirmed that the (R)-(+)-SAMe isomer content was lower than 5%, and that the (S)-(+)-SAMe isomer exceeded 95%.

Example 2

As per example 1, but the biomass is activated twice. 14.2% w/dry w of total SAMe is obtained, of which 4.3% w/w is (R)-(+)-SAMe isomer and 95.7% is (S)-(+)-SAMe isomer.

Example 3

As per examples 1 and 2, but the biomass undergoes a third enrichment process, producing 15.1% w/dry w of total SAMe, of which 4.4% (R)-(+)-SAMe isomer and 95.6% w/dry weight of (S)-(+)-SAMe.

Example 4

As per examples 1-3, wherein the dried biomass is microencapsulated by adding bentonite and drying at 32° C. (±2° C.) under vacuum at 5 mbars, ground to a fine powder and added to the granulate for microencapsulation as indicated below:

|  | g % |
|---|---|
| *Saccharomyces cerevisiae* powder | 10 |
| Mannitol | 50 |
| Microcrystalline cellulose | 10 |
| Colloidal silicon dioxide | 2 |
| Mg stearate | 3 |
| Glycerol behenate 888 | 5 |
| Hydrogenated vegetable fat (Biogapress Vegetal 8M297, GATTEFOSSÈ) | 20 |

The powder is suitably mixed with all the components except for the hydrogenated vegetable fat. This mixture is used to make tablets with a 20-25 mm diameter which are then granulated in an oscillating granulator to produce 300-1500 micron granules. The granule is coated with melted vegetable fat using a recirculating screw mixer and left to cool at ambient temperature, producing 500-1600 micron microcapsules containing 3.0 (±5%)×$10^9$ CFU/g.

Example 5

The yeast *Saccharomyces cerevisiae* GNL-24/497-(DB-VPG 8P) was prepared and dried as described in example 1.

The dried biomass was subjected to a stability program at ambient temperature (T=25±2° C. and RH=60±5%).

For analysis purposes, the cells were mechanically lysed at +4° C.

The table below shows the results obtained:

| SAMPLE Time in days | KF % | (S)-(+)-SAMe % CONTENT | (R)-(+)SAMe % CONTENT |
|---|---|---|---|
| 0 | 0.40 (±0.05) | 94.50 (±0.1) | 5.50 (±0.1) |
| 15 | 0.40 (±0.05) | 94.10 (±0.1) | 5.90 (±0.1) |
| 45 | 0.40 (±0.05) | 94.10 (±0.1) | 5.90 (±0.1) |
| 75 | 0.40 (±0.05) | 94.00 (±0.1) | 6.00 (±0.1) |
| 100 | 0.40 (±0.05) | 94.10 (±0.1) | 5.90 (±0.1) |
| 120 | 0.42 (±0.05) | 93.80 (±0.1) | 6.20 (±0.1) |
| 150 | 0.42 (±0.05) | 94.00 (±0.1) | 6.00 (±0.1) |
| 180 | 0.46 (±0.05) | 93.90 (±0.1) | 6.10 (±0.1) |

Example 6

Tablets having the following composition were prepared with the dried biomass, as indicated in examples 1, 2, 3, 4, according to known techniques:

| CONSTITUENTS | FUNCTION | QUANTITY |
|---|---|---|
| Dried cells | Active constituent ≥200 mg Excipients: core | 1350 mg |
| Microcrystalline cellulose | Binder | 86.00 mg |
| Colloidal silicon dioxide | Absorbent | 7.00 mg |
| Glycerol behenate | Lubricant | 20.00 mg |
| Magnesium stearate | Anti-adherent agent | 7.00 mg |
| Total weight | | 1470 mg |

Example 7

Tablets having the following composition were prepared with the dried biomass, as indicated in examples 1, 2, 3, 4, according to known techniques:

Composition Per Tablet

| CONSTITUENTS | FUNCTION | QUANTITY |
|---|---|---|
| Dried cells | Active constituent ≥200 mg Excipients: core | 1350 mg |
| Microcrystalline cellulose | Binder | 86.00 mg |
| Colloidal silicon dioxide | Absorbent | 7.00 mg |
| Glycerol behenate | Lubricant | 20.00 mg |
| Magnesium stearate | Anti-adherent agent Excipients (spinning) | 7.00 mg |
| Biogapress ® vegetal (Glyceryl glycerol palmitost.) | Protector | 11.20 mg |
| Labrafac ® CC * | Protector | 11.20 mg |
| Eudragit L30D-55 ** | Filming agent | 43.20 mg |
| Titanium dioxide | Opacifier | 7.20 mg |
| Talc | Anti-adherent agent | 14.25 mg |
| Colloidal silicon dioxide (Aerosol 200) | Desiccant | 1.00 mg |

| CONSTITUENTS | FUNCTION | QUANTITY |
| --- | --- | --- |
| Triethyl citrate | Plasticiser | 11.55 mg |
| Tartrazine yellow | Colouring | 0.08 mg |
| Total weight | | 1569.68 mg |

\* LABRAFAC (chain triglycerides)
\*\* EUDRAGIT (copolymer of methacrylic acid)
\*\*\* FD (tartrazine)

Example 8

The tablets referred to in example 7 were subjected to the gastroresistance test according to the European Pharmacopoeia, using the PHARMATEST PTL-5 disintegrator apparatus. After 1 hour the tablets were totally intact.

The invention claimed is:

1. Microencapsulated cells of isolated *Saccharomyces cerevisiae* strain deposited in the DBVPG collection under number DBVPG 8 P.

2. Cells as claimed in claim 1, wherein the microencapsulated cells are dried.

3. Cells as claimed in claim 1, in microencapsulated form as microcapsules having a diameter from about 500 to about 1600 microns.

4. Cells as claimed in claim 1, having a total S-adenosyl-L-methionine (SAMe) content of 7%-20% w/dry w.

5. Cells as claimed in claim 2 obtained by
a) isolating cells of *S. cerevisiae* DBVPG 8 P from a sample of culture broth taken from industrial fermentation at a pre-stationary stage;
b) growing the isolated cells of *S. cerevisiae* DBVPG 8 P obtained in step a);
c) microencapsulating the isolated cells of *S. cerevisiae* DBVPG 8 P; and
d) drying the microencapsulated cells of *S. cerevisiae* DBVPG 8 P at temperatures ranging from 20 to 40° C., optionally under reduced pressure, in the absence of stabilizing agents.

6. Cells as claimed in claim 4, wherein in the total SAMe content, (R)-(+)-S-adenosyl-L-methionine is present in a quantity lower than or equal to 10% of (S)-(+)-S-adenosyl-L-methionine.

7. Cells as claimed in claim 1 obtained by
a) isolating cells of *S. cerevisiae* DBVPG 8 P from a sample of culture broth taken from industrial fermentation at a pre-stationary stage;
b) growing the isolated cells of *S. cerevisiae* DBVPG 8 P obtained in step a); and
c) microencapsulating the isolated cells of *S. cerevisiae* DBVPG 8 P.

\* \* \* \* \*